United States Patent [19]
Aubert

[11] Patent Number: 5,272,292
[45] Date of Patent: Dec. 21, 1993

[54] IRREVERSIBLE ARRANGEMENT FOR INTERRUPTING THE FUNCTIONING OF AN APPARATUS CONTROLLED BY AN ELECTRONIC SYSTEM

[75] Inventor: Christophe Aubert, Fontainemelon, Switzerland

[73] Assignee: SMH Management Services AG, Biel, Switzerland

[21] Appl. No.: 866,983

[22] Filed: Apr. 10, 1992

[30] Foreign Application Priority Data

Apr. 19, 1991 [FR] France .................. 91 04966

[51] Int. Cl.⁵ ........................................ H01H 85/00
[52] U.S. Cl. ................................ 200/61.08; 200/300
[58] Field of Search .................... 200/61.05, 300; 561/395, 397; 340/303, 590; 60/632-638

[56] References Cited

U.S. PATENT DOCUMENTS

| | | | |
|---|---|---|---|
| 4,062,290 | 12/1977 | Mayer | 102/70.2 R |
| 4,527,025 | 7/1985 | Patrichi et al. | 200/61.08 |

FOREIGN PATENT DOCUMENTS

| | | |
|---|---|---|
| 0065826 | 4/1982 | European Pat. Off. |
| 0447909 | 3/1991 | European Pat. Off. |
| 2949914 | 12/1979 | Fed. Rep. of Germany |
| 1582980 | 10/1969 | France |
| 2659856 | 3/1990 | France |
| 9003869 | 3/1990 | France |
| 2046536 | 11/1980 | United Kingdom |

*Primary Examiner*—Howard L. Williams
*Assistant Examiner*—Michael A. Friedhofer
*Attorney, Agent, or Firm*—Pollock, Vande Sande & Priddy

[57] ABSTRACT

The present invention concerns an irreversible arrangement for interrupting the functioning of an apparatus controlled by an electronic system. The purpose of such invention is to provide an arrangement which can be easily manipulated by an inexperienced user and which permits him to interrupt the functioning of the apparatus immediately and definitely. This purpose is attained with the help of of an irreversible arrangement for interrupting the functioning of an apparatus (1) controlled by an electronic system (15), characterized in that it comprises at least one interruption element (17) movable between a rest position allowing the functioning of said apparatus (1) and an interruption position in which it brings about the irreversible interruption of the functioning of said apparatus (1) by breaking an essential element of said electronic system (15) such essential element being necessary for the functioning of the apparatus (1). This arrangement is more specifically intended for medical apparatus.

17 Claims, 3 Drawing Sheets

IRREVERSIBLE ARRANGEMENT FOR INTERRUPTING THE FUNCTIONING OF AN APPARATUS CONTROLLED BY AN ELECTRONIC SYSTEM

The present invention concerns an irreversible arrangement for interrupting the functioning of an apparatus controlled by an electronic system, in particular a medical apparatus, for example a medical pump.

BACKGROUND OF THE INVENTION

Medical pumps have been known for several years and enable the administration of medications to a patient in small doses and continuously. Such pumps are of small dimensions and are devised so as to be carried by the patient and to have an autonomy of several days, which permits the patient to be no longer confined to bed and to circulate freely. In particular such pumps permit the patient to live at home without being permanently under medical observation.

The absence of medical personnel observing such patients and the good functioning of their pumps has led the health authorities to require that such pumps be provided with numerous systems of security.

Thus, such pumps are generally programmed in advance in order to stop functioning at the end of a given time and furthermore all misfunctioning of the pump such as obstruction of a channel or appearance of excessive pressure is detected and brings about the immediate stoppage of the pump.

Nevertheless, it would be desirable to provide complementary security arrangements. In effect, the invalid carrying the pump may feel indisposed at a given instant and wish to stop his pump, even if the latter is functioning in a perfectly correct manner. However, it cannot be envisaged to provide a simple stop/go switch for then the invalid, after having stopped the pump, could put it back into operation whenever he so desired without following the dosage and the administration sequence of the medication provided by the medical practitioner. This would be contrary to the mandatory security standards and to the requirements of the medical corps and it is why it is necessary to have irreversible means for interrupting the functioning of the pump.

The purpose of the invention is to respond to these imperatives.

SUMMARY OF THE INVENTION

To this end, the invention concerns an irreversible arrangement for interrupting the functioning of an apparatus controlled by an electronic system.

According to the characteristics of the invention, such arrangement comprises at least one interruption element movable between a rest position allowing the functioning of the apparatus and an interruption position in which it brings about the irreversible interruption of the functioning of the apparatus by breaking an essential element of the electronic system, such essential element being necessary for the functioning of the apparatus.

Thanks to this arrangement, the user may break a vital element of the electronic system in bringing about the absolutely irreversible stoppage of the apparatus, in particular a medical pump. Thus one obtains the sought-for security effect, in particular in the medical domain, since on the one hand the apparatus stops immediately and on the other hand the user may not put it back into operation. Furthermore, it is practically impossible for an average user to repair the damage caused to the electronic system. The apparatus thus may not be diverted to other ends.

In the preferred embodiment of the invention, the electronic system comprises a printed circuit.

According to other characteristics of the invention, the interruption element comprises a piston sliding within an open-ended orifice bounded by a casing, such piston comprising a central body, a rupturing end placed in the vicinity of said printed circuit and a piston head on which the user may act in order to displace said piston from the rest position to the interruption position. Furthermore, the rupturing end is provided with a projecting portion designed to break said printed circuit when the piston is displaced into the rupturing position.

This arrangement is thus extremely simple to use by an inexperienced user who has simply to exert a pressure on said piston in order to displace the latter.

Finally, the piston head is surmounted by protection means preventing access to said piston head and exhibiting a zone of lesser resistance which may be broken in order to permit access to the piston head.

Thanks to this characteristic, the interruption means may not be triggered in an involuntary manner by the user. This is particularly interesting when the apparatus is a medical pump which the user wears permanently on his person and which is in contact with the body.

The invention will be better understood upon reading the following description of an embodiment thereof given by way of illustrative example, such description being formulated in respect of the attached drawings.

DESCRIPTION OF THE PREFERRED EMBODIMENT

Figure 1:
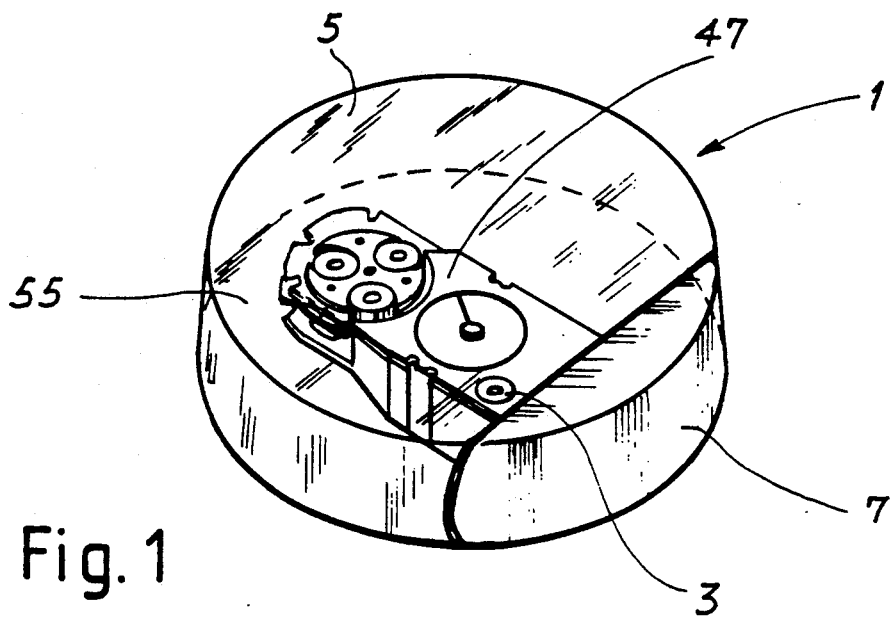
FIG. 1 shows a perspective view of an apparatus in two assembled parts provided with an interruption arrangement according to the invention.

FIG. 1 illustrates an apparatus 1 (it concerns in this case a medical peristaltic pump), provided with an irreversible interruption arrangement 3 according to the invention. Such apparatus 1 in two parts comprises a reservoir module 5 and a motor module 7. A practical example of such peristaltic pump is described in the patent application FR-90 03869. At the same time, it is evident that such pump is not a limiting example of the type of apparatus which may be provided with the interruption arrangement according to the invention. The interruption arrangement may be adapted for any apparatus whatsoever, in particular medical, which necessitates an irreversible emergency stop arrangement.

Figure 2:
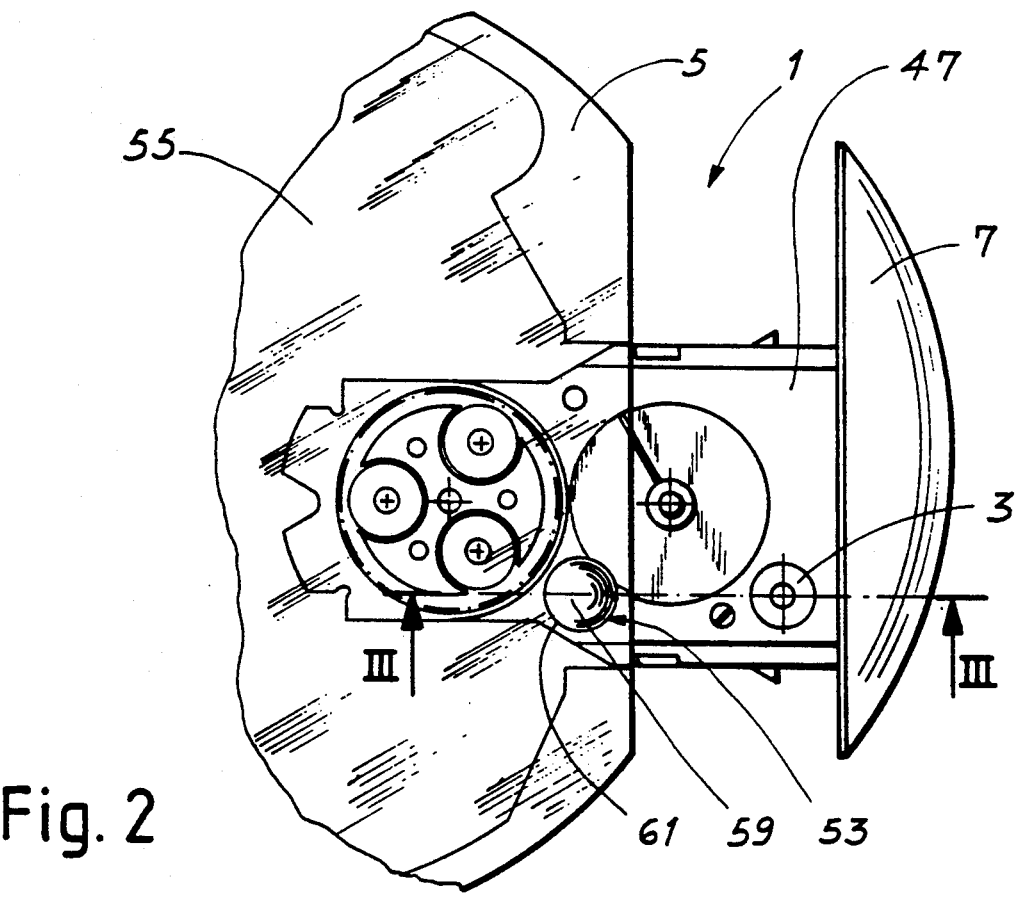
FIG. 2 is a top view of the apparatus of figure 1, the two parts of such apparatus not being completely assembled.

As illustrated in FIG. 2, the motor module 7 provided with the irreversible interruption arrangement 3 according to the invention is fitted like a drawer within a cavity of the reservoir module 5.

Figure 3:
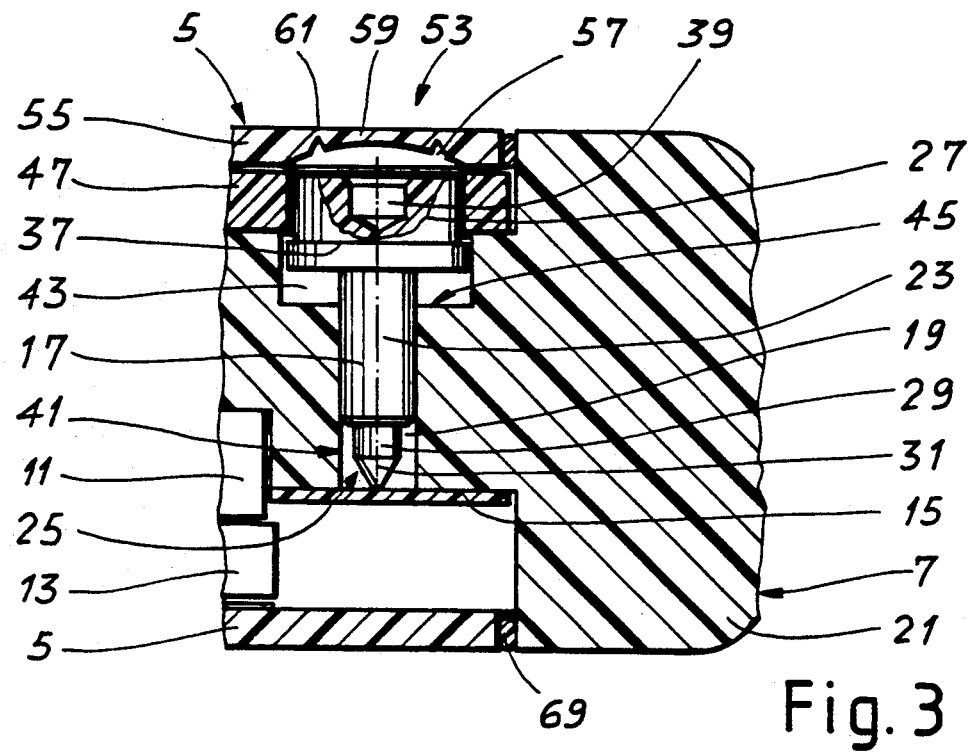
FIG. 3 is a cross-section view along line III—III of FIG. 2, but with the two parts of the apparatus assembled and the interruption arrangement according to the invention being in the rest position.
Figure 4:
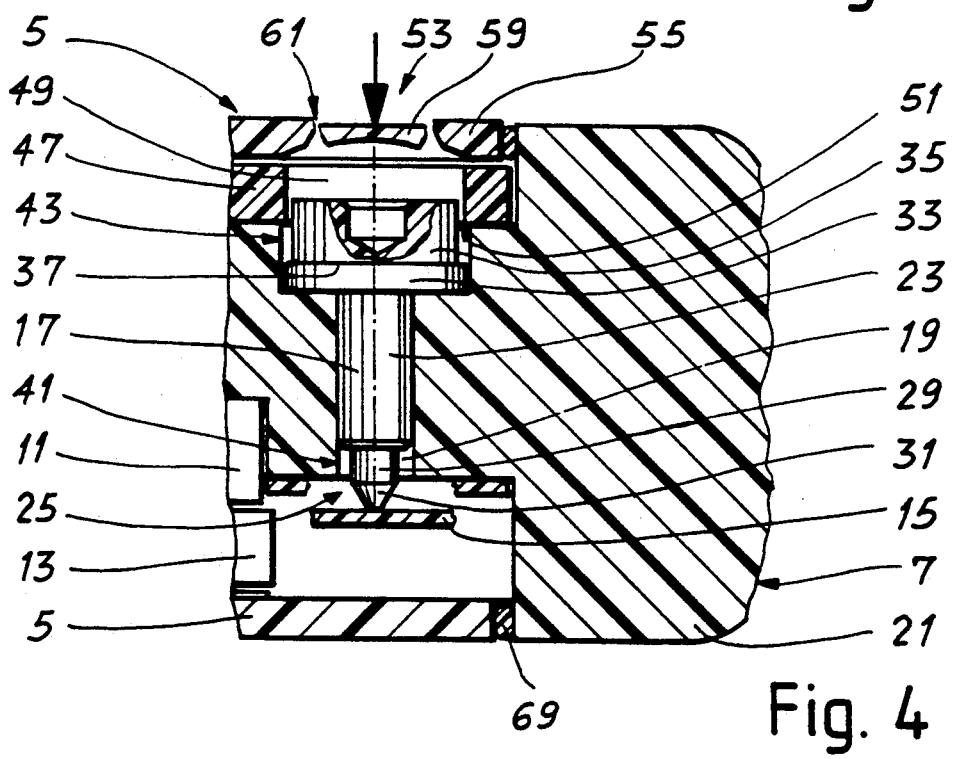
FIG. 4 is identical to FIG. 3 except that the interruption arrangement is in the interruption position.

The functioning of apparatus 1 takes place thanks to a motor 11 fed by an energy source 13 and controlled by a printed circuit 15 seen in cross-section on figures 3 and 4.

Such interruption arrangement 3 comprises at least one interruption element 17 movable between a first rest position (illustrated in FIG. 3) enabling the normal functioning of said apparatus and a second interruption position (illustrated in FIG. 4) in which an essential element of said printed circuit 15 is broken.

More precisely, the interruption element 17 takes the form of a piston sliding within an open-ended orifice 19 bounded by a casing 21 integrally formed with the motor module 7. Such piston 17 comprises a central body 23, a rupturing end 25 placed in the vicinity of said printed circuit 15 and a piston head 27. Preferably, the central body 23 and the open-ended orifice 19 are cylindrical.

The rupturing end 25 comprises a cylindrical part 29 having a diameter less than that of the central body 23, such part 29 ending by a projecting portion 31 designed to break an essential element of the printed circuit 15. In the embodiment shown here, such projecting portion 31 is substantially conical. Nevertheless, it could also have any other form, preferably pointed, permitting the rupturing of an essential element of said printed circuit when piston 17 is displaced.

The head of piston 27 comprises a lower portion 33 coupled to the central body 23 and an upper portion 35 of a diameter less than portion 33 defining, together with such latter, an annular shoulder 37. Furthermore, the upper portion 35 exhibits on its free end surface a cavity 39 designed to accommodate a tool which may cause the piston 17 to slide. Such cavity 39 is coaxial with piston 17.

Piston 17 and the open-ended orifice 19 at the level of the printed circuit 15 are arranged along an axis substantially perpendicular to the plane of said printed circuit.

The open-ended orifice 19 comprises, successively from the printed circuit 15 up to the exterior, an elongated slideway portion 41 of a diameter very slightly greater than that of the body of piston 23 and a chamber 43 of a diameter very slightly greater than the lower portion 33 of the piston head 37. Such small differences in diameter permit sliding of piston 17.

Chamber 43 is of a diameter greater than that of the slideway portion 41 and thus defines an annular shoulder 45.

During assembly, the piston 17 is introduced to the interior of the open-ended orifice 19 and a plate 47 exhibiting a circular opening 49 coaxial with orifice 19 is secured above such orifice. The diameter of such opening 49 is slightly greater than the diameter of the upper portion 35 of the head of piston 27 and thus such part 35 may slide freely in such opening 49.

Furthermore, the diameter of such opening 49 is slightly less than that of chamber 43 and defines with the latter an annular abutment 51.

According to a variant of the embodiment, the interruption arrangement according to the invention may also comprise protection means 53 for the piston head 27. In the case of the apparatus shown on FIGS. 1 and 2, such protection means 53 are provided in the upper face 55 of the reservoir module 5 formed of plastic material. Such protection means 53 are devised in order to be placed just above the head of the piston 27 when the motor module 7 is fitted within the reservoir module 5.

Nevertheless, when the apparatus provided with the interruption arrangement according to the invention is in one single piece, one may provide a final step during the assembly, in the course of which there is arranged a plate of plastic material forming the protection means above the piston head 27 and plate 47.

The lower surface of the upper face 55 of the reservoir module 5 exhibits a groove 57 bounding a circular central zone 59 and defining a zone 61 of lesser resistance.

Figure 5:
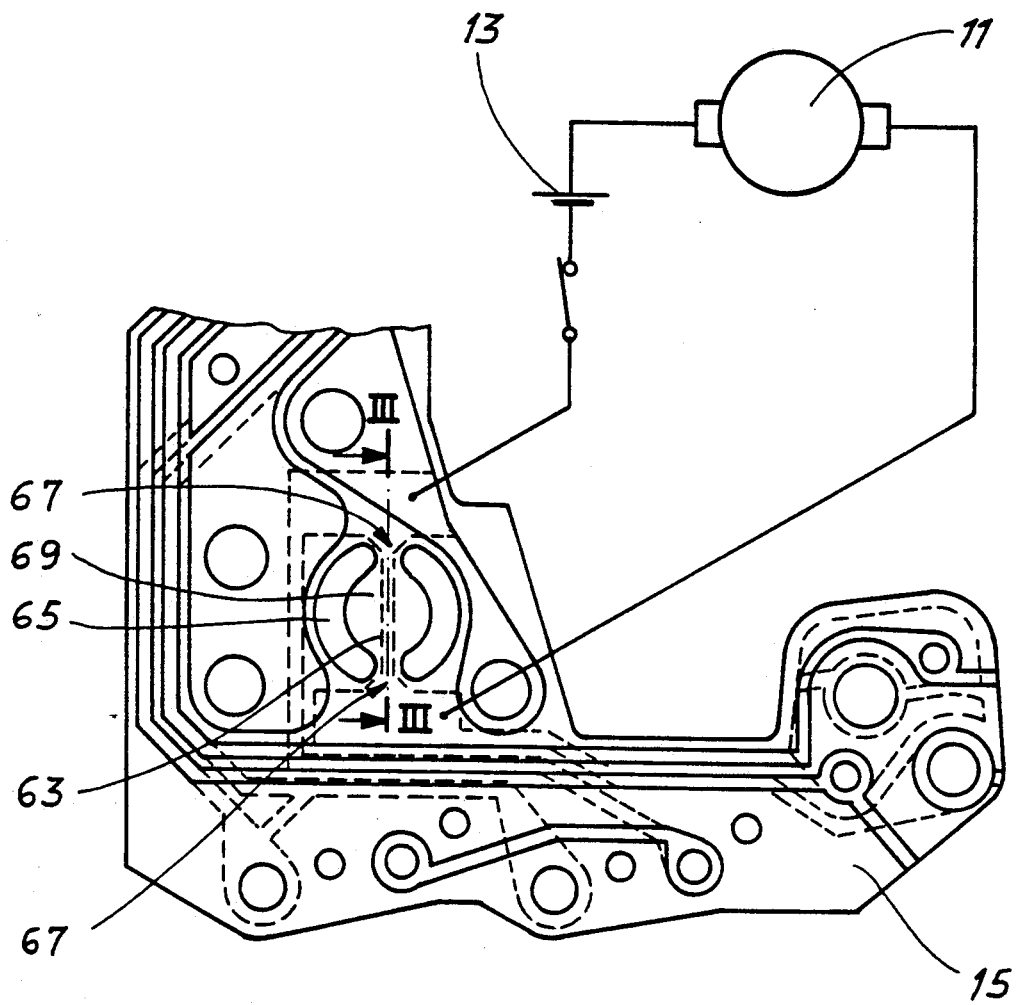
FIG. 5 shows a top partial view of the printed circuit used with the interruption arrangement according to the invention.

FIG. 5 illustrates an embodiment of the printed circuit 15 partially shown.

Such printed circuit 15 exhibits a plurality of tracks 63 an example of the configuration of which is shown on FIG. 5.

The printed circuit 15 according to the invention exhibits two hollows 65 in the form of a bean, arranged face-to-face on either side of one or several tracks 63 which one wishes to break and which are essential to the functioning of the apparatus controlled by circuit 15. Effectively, such tracks 63 enable connecting the motor 11 to its feeding source 13 as is schematically shown on FIG. 5.

Such hollows 65 define between them two zones 67 of lesser resistance and a substantially circular area 69 traversed by said tracks 63. Piston 17 is arranged in a manner such that its rupturing end is facing such area 69 and zones 67 and more precisely such that the projecting portion 31 is posed substantially in the center of area 69.

According to another variant one may provide the arrangement of hollows 65, not around tracks 63, but around another essential element of the printed circuit enabling functioning of apparatus 1.

The functioning of the interruption arrangement according to the invention will now be described in greater detail.

When the user of an apparatus provided with an interruption arrangement according to the invention, for example an invalid carrying a medical pump, wishes to stop the functioning of said pump, he employs a pointed object such as a pencil or a thumb tack in order to break the circular zone 59 and push in piston 17. The latter is displaced from the rest position shown on FIG. 3 to the interruption position shown on FIG. 4 where the projecting portion 31 of said piston breaks one or several tracks 63 of the printed circuit 15. Such rupture is facilitated by the zones of lesser resistance 67.

The travel of piston 17 is limited by shoulder 45 which serves as abutment for the head of piston 27.

In addition, it is observed that in the rest position illustrated in FIG. 3, the piston rests on the printed circuit 15. Nevertheless, if in the course of manipulation the apparatus is turned over by the user through 180°, the lower portion 33 of the piston head is retained by the annular abutment 51 and piston 17 does not run the risk of coming out of the open-ended orifice 19.

Finally, it will be noted that the protection means 53 enable also to assure sealing of the interruption arrangement 3. Effectively, generally there is provided a seal 69 between the reservoir module 5 and the motor module 7. Such seal 69, associated with the protection means 53, enables avoiding the entry of water for instance into the open-ended orifice 19. This is particularly useful in the case of a medical pump which the user continues to wear even while washing himself.

What I claim is:

1. An irreversible arrangement for interrupting the functioning of an apparatus controlled by an electronic system, said arrangement comprising at least one interruption member movable between a rest position permitting the functioning of said apparatus and an interruption position in which said member brings about the irreversible interruption of the functioning of said apparatus by breaking an essential element of said electronic system, said essential element being necessary for the functioning of said apparatus, and said interruption member comprising a piston sliding within an open-ended orifice bounded by a casing, said piston comprising:
   a central body,
   a rupturing end placed in the vicinity of said essential element, and
   a piston head on which a user may act in order to displace said piston from the rest position to the interruption position.

2. An irreversible arrangement for interrupting the functioning of an apparatus as set forth in claim 1 wherein said electronic system comprises at least one printed circuit which includes the essential element.

3. An irreversible arrangement for interrupting the functioning of an apparatus as set forth in claim 2 wherein the essential element comprises at least one track of said printed circuit, said track providing an essential connection between a motor assuring the functioning of the apparatus and an energy source feeding said motor.

4. An irreversible arrangement for interrupting the functioning of an apparatus as set forth in claim 2 wherein the rupturing end is provided with a projecting portion designed for breaking the essential element of said printed circuit when the piston is displaced into the interruption position.

5. An irreversible arrangement for interrupting the functioning of an apparatus as set forth in claim 4 wherein the portion projecting from the rupturing end is substantially conical.

6. An irreversible arrangement for interrupting the functioning of an apparatus as set forth in claim 2 wherein the interruption piston is to slide along an axis substantially perpendicular to the plane of said printed circuit.

7. An irreversible arrangement for interrupting the functioning of an apparatus as set forth in claim 1 wherein the head of the piston has a lateral dimension greater than a corresponding lateral dimension of the central body and wherein the open-ended orifice is enlarged at one of its ends in order to define a shoulder cooperating wit the head of the piston in order to limit the travel of said piston.

8. An irreversible arrangement for interrupting the functioning of an apparatus as set forth in claim 1 wherein the head of the piston has a free end with a cavity designed to accommodate a tool to effect sliding of said piston.

9. An irreversible arrangement for interrupting the functioning of an apparatus as set forth in claim 1 wherein the central body of the piston and the open-ended orifice are cylindrical.

10. An irreversible arrangement for interrupting the functioning of an apparatus as set forth in claim 1 wherein the head of the piston is surmounted by protection means preventing access to said piston head an comprising a zone of lesser resistance which may be broken to enable access to the head of the piston.

11. An irreversible arrangement according to claim 2 wherein said printed circuit has at least one zone of lesser rupture resistance provided around said essential element, and where in the interruption member is placed facing size zone of lesser rupture resistance.

12. An irreversible arrangement as set forth in claim 11 wherein said apparatus is a peristaltic pump.

13. An apparatus comprising:
    a casing;
    an electronic system in said casing and comprising an essential element which is necessary for operation of said apparatus; and,
    an arrangement for user controlled, irreversible interruption of the operation of said apparatus, said arrangement comprising at least one interruption member mounted in said casing so as to be movable by a user acting thereon between a rest position in which operation of said apparatus is allowed and an interruption position in which said interruption member is capable of instantaneously breaking said essential element of said electronic system.

14. An apparatus as set forth in claim 13, wherein said electronic system comprises at least one printed circuit which includes said essential element.

15. An apparatus as set forth in claim 14 wherein said printed circuit has at least one zone of lesser rupture resistance provided around said essential element, and wherein the interruption member is place facing said zone of lesser rupture resistance.

16. An apparatus as set forth in claim 14 further comprising:
    a motor mounted in said casing for assuring the operation of said apparatus, and
    an energy source also mounted in said casing for supplying energy to said motor; and
    wherein said printed circuit comprises at least one conductive track connected between said motor and said energy source, said track constituting said essential element.

17. An apparatus as set forth in claim 16 wherein said apparatus is a peristaltic pump.

* * * * *

UNITED STATES PATENT AND TRADEMARK OFFICE
CERTIFICATE OF CORRECTION

PATENT NO. : 5,272,292
DATED : December 21, 1993
INVENTOR(S) : CHRISTOPHE AUBERT It is certified that error appears in the above-identified patent and that said Letters Patent is hereby corrected as shown below:

```
Column 6, line 11, after "head" change "an" to --and--;
         line 17, change "where in" to --wherein--;
         line 18, change "size" to --said--; and
         line 42, change "place" to --placed--.
```

Signed and Sealed this

Third Day of May, 1994

Attest:

BRUCE LEHMAN

Attesting Officer

Commissioner of Patents and Trademarks